US010022060B2

(12) United States Patent
Nearing et al.

(10) Patent No.: US 10,022,060 B2
(45) Date of Patent: *Jul. 17, 2018

(54) HIGH THROUGHPUT ARRHYTHMIA RISK ASSESSMENT USING MULTILEAD RESIDUA SIGNALS

(71) Applicant: BETH ISRAEL DEACONESS MEDICAL CENTER, INC., Boston, MA (US)

(72) Inventors: Bruce D. Nearing, North Reading, MA (US); Richard L. Verrier, Wellesley Hills, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 170 days.

This patent is subject to a terminal disclaimer.

(21) Appl. No.: 14/734,966

(22) Filed: Jun. 9, 2015

(65) Prior Publication Data

US 2015/0272462 A1    Oct. 1, 2015

Related U.S. Application Data

(63) Continuation-in-part of application No. 13/624,544, filed on Sep. 21, 2012, now Pat. No. 9,060,699.

(51) Int. Cl.
*A61B 5/04* (2006.01)
*A61B 5/0456* (2006.01)
(Continued)

(52) U.S. Cl.
CPC ........ *A61B 5/04012* (2013.01); *A61B 5/0452* (2013.01); *A61B 5/0456* (2013.01);
(Continued)

(58) Field of Classification Search
CPC ... A61B 5/0452; A61B 5/0464; A61B 5/0468; A61B 5/0472; A61B 5/04012;
(Continued)

(56) References Cited

U.S. PATENT DOCUMENTS 5,560,370 A    10/1996   Verrier et al.
5,921,940 A     7/1999   Verrier et al.
(Continued)

FOREIGN PATENT DOCUMENTS

WO    WO 2008/008361 A2    1/2008

OTHER PUBLICATIONS

Nearing, Bruce D. et al. "Crescendo in Depolarization and Repolarization Heterogeneity Heralds Development of Ventricular Tachycardia in Hospitalized Patients with Decompensated Heart Failure," Circ. Arrythm Electrophysiol., vol. 5, pp. 84-90, Dec. 8, 2011.

(Continued)

*Primary Examiner* — Amanda Patton
(74) *Attorney, Agent, or Firm* — Sterne, Kessler, Goldstein & Fox P.L.L.C.

(57) ABSTRACT

A method and system for high-throughput prediction of the onset of heart arrhythmias observes trends in abnormal or pathologic morphology of the electrocardiogram (ECG). A first set of ECG signals is monitored from a patient. A baseline measurement is generated from the monitored first set of ECG signals to contain nonpathologic ECG morphologies in each lead. A second set of ECG signals is monitored from the patient and a second baseline measurement is generated from the second set of ECG signals. A residuum signal is generated for each lead based on the baseline measurement and the second baseline measurement. The residuum signals are averaged across the leads. R-wave heterogeneity, T-wave heterogeneity, P-wave heterogeneity, or ST-segment heterogeneity or other indicators of arrhythmia risk or myocardial ischemia are quantified based on the generated residuum signals and the averaged residuum signal.

38 Claims, 12 Drawing Sheets

(51) Int. Cl.
  *A61B 5/00* (2006.01)
  *A61B 5/0452* (2006.01)
(52) U.S. Cl.
  CPC ........ *A61B 5/04525* (2013.01); *A61B 5/7246* (2013.01); *A61B 5/7275* (2013.01); *A61B 5/7278* (2013.01)
(58) Field of Classification Search
  CPC . A61B 5/04525; A61B 5/0456; A61B 5/7246; A61B 5/7275; A61B 5/7278
  USPC .......................................................... 600/516
  See application file for complete search history.

(56) References Cited

U.S. PATENT DOCUMENTS

| | | | |
|---|---|---|---|
| 6,035,231 | A | 3/2000 | Sornmo et al. |
| 6,169,919 | B1 | 1/2001 | Nearing et al. |
| 6,178,347 | B1 | 1/2001 | Olsson |
| 7,174,204 | B2 | 2/2007 | Hadley et al. |
| 9,060,699 | B2 | 6/2015 | Nearing et al. |
| 2002/0120206 | A1 | 8/2002 | Taha et al. |
| 2002/0138013 | A1 | 9/2002 | Guerrero et al. |
| 2002/0143265 | A1 | 10/2002 | Ackerman et al. |
| 2002/0183639 | A1 | 12/2002 | Sweeney et al. |
| 2005/0010122 | A1 | 1/2005 | Nearing et al. |
| 2007/0010752 | A1 | 1/2007 | Korhonen |
| 2007/0088395 | A1 | 4/2007 | Province et al. |
| 2009/0281440 | A1 | 11/2009 | Farazi et al. |

OTHER PUBLICATIONS

Acar, B., et al., "Spatial, temporal and wavefront direction characteristics of 12-lead T-wave morphology," Medical & Biological Engineering & Computing 37(5):574-584, Springer, Germany (1999).

Bonizzi, P., et al., "Noninvasive Assessment of the Complexity and Stationarity of the Atrial Wavefront Patterns During Atrial Fibrillation," IEEE Transactions on Biomedical Engineering, 57(9): 2147-2157, IEEE Service Center, United States (2010).

International Search Report for International Application No. PCT/US2013/060982, European Patent Office, Netherlands, dated Aug. 1, 2014.

Legarreta, I.R., et al., "Common spatial pattern: An improved method for atrial fibrillation wave extraction," Computers in Cardiology, 2007:501-504, IEEE, United States (2007).

Malik, M., et al., "QT Dispersion Does Not Represent Electrocardiographic Interlead Heterogeneity of Ventricular Repolarization," Journal of Cardiovascular Electrophysiology, 11(8):835-843 (2000).

Markus, Z., et al., "Analysis of T-Wave Morphology From the 12-lead Electrocardiogram for Prediction of Long-Term Prognosis in male US veterans," Circulation, 105(9):1066-1070, Lippincot Williams and Wilkins, United States (2002).

Nearing, B.D., "Tracking cardiac electrical instability by computing interlead heterogeneity of T-wave morphology," Journal of Applied Physiology, 95(6):2265-2272, American Physiological Society, United States (2003).

Nearing, B.D., et al., "Modified moving average analysis of T-wave alternans to predict ventricular fibrillation with high accuracy," Journal of Applied Physiology, 92(2):541-549, American Physiological Society, United States (2002).

Pueyo, E., et al., "Cardiac repolarization analysis using the surface electrocardiogram," Philosophical Transactions of the Royal Society, A 367, 213-233 (2009).

Nearing, B., et al., "Multilead Template-Derived Residua of Surface ECGS for Quantitative Assessment of Arrhythmia Risk," Annals of Non-Invasive Electrocardiology, 2015; 20 (3):273-281.

HIGH THROUGHPUT ARRHYTHMIA RISK ASSESSMENT USING MULTILEAD RESIDUA SIGNALS

CROSS-REFERENCE TO RELATED APPLICATIONS

This application shares common subject matter with and is related to commonly owned U.S. patent application Ser. No. 13/624,544, filed Sep. 21, 2012, and titled "Multilead ECG Template-Derived Residua for Arrhythmia Risk Assessment," (now U.S. Patent No. 9,060,699), which is incorporated herein by reference in its entirety.

STATEMENT REGARDING FEDERALLY-SPONSORED RESEARCH AND DEVELOPMENT

This invention was made with government support under HL085720 awarded by the National Institutes of Health. The government has certain rights in the invention.

BACKGROUND OF THE INVENTION

Field of the Invention

Embodiments herein relate to systems and methods for determining potential health risks by analyzing electrocardiograms (ECG).

Background Art

Heart rhythm abnormalities, referred to as "arrhythmias" and originating from both the atria and ventricles, constitute a predisposing condition leading to significant morbidity and mortality in the U.S. population. Atrial fibrillation affects 2.2 million U.S. citizens and accounts for 500,000 hospitalizations annually. Sudden cardiac death due to ventricular arrhythmias accounts for 310,000 U.S. deaths each year. Thus, there is a great need to improve arrhythmia risk assessment, which can lead to better diagnosis of underlying disease and help to guide therapy.

The public health impact of arrhythmias is underscored by the prevalence of heart failure. This condition in which atrial and ventricular arrhythmias co-exist affects over five million Americans, with hospitalization of more than one million patients for decompensated heart failure yearly. These individuals experience a high degree of ventricular ectopy and spontaneous ventricular arrhythmias. Sudden cardiac death constitutes a high proportion of deaths in the heart failure population (58% in New York Heart Association [NYHA] class III and 33% in NYHA class IV). However, no standard electrocardiographic markers, including ventricular ectopy or arrhythmias, have proven to be reliable indicators of life-threatening cardiac arrhythmias.

Considerable evidence indicates that analysis of subtle variations in ECG signal morphology, including T-wave heterogeneity, T-wave variability, and T-wave alternans (TWA) may reveal arrhythmia risk. However, intrinsic morphology differences among ECG signals in the standard leads may mask arrhythmogenic ECG morphology changes. Complex influences including impedance and ECG vector cancellation of electrocardiographic signals contribute to differences in the projected amplitude of the signals to the body surface. Thus, microvolt levels of ECG morphology changes that are associated with disease states such as ischemic episodes, acute coronary syndrome, or heart failure may be difficult and imprecise to detect.

BRIEF SUMMARY OF THE INVENTION

Example methods and systems are described herein for embodying a high-throughput approach to isolating abnormal ECG signals to capture and measure morphologic ECG changes that may be associated with lethal cardiac arrhythmias.

In an embodiment, an example method is described. The method includes receiving a first set of electrocardiogram (ECG) signals from spatially separated leads; generating a median beat signal associated with the morphology of each ECG signal of the first set of ECG signals; receiving a second set of ECG signals from spatially separated leads; generating a second median beat signal associated with the morphology of each ECG signal of the second set of ECG signals; calculating, for each lead, a residuum signal based on the first and second median beat signals; averaging the residuum signals across the leads to produce an averaged residuum signal; and quantifying ECG characteristics based on the residuum signals and the averaged residuum signal. The quantified ECG characteristics are associated with arrhythmia risk. For example, R-wave heterogeneity and/or T-wave heterogeneity may be quantified based on this method. This method may also be used to quantify P-wave changes indicative of risk of atrial arrhythmias or ST-segment changes among spatially separated leads to identify regions of myocardial ischemia.

In another embodiment, an electrocardiogram system is described. The system includes an input module and a processor. The input module receives ECG signals from spatially separated leads. The processor is designed to generate a median beat signal associated with the morphology of each ECG signal of a first set of ECG signals from the spatially separated leads. The processor further generates a second median beat signal associated with the morphology of each ECG signal of a second set of ECG signals from the spatially separated leads. The processor also calculates, for each lead, a residuum signal based on the median beat signal and the second median beat signal. The processor also averages the residuum signals across the leads to produce an averaged residuum signal and quantifies ECG characteristics based on the residuum signals and the averaged residuum signal, wherein the characteristics are associated with arrhythmia risk, as described herein.

In another embodiment, a computer program product stored on a computer readable media includes a set of instructions that, when executed by a computer device, perform the steps of the above described method.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
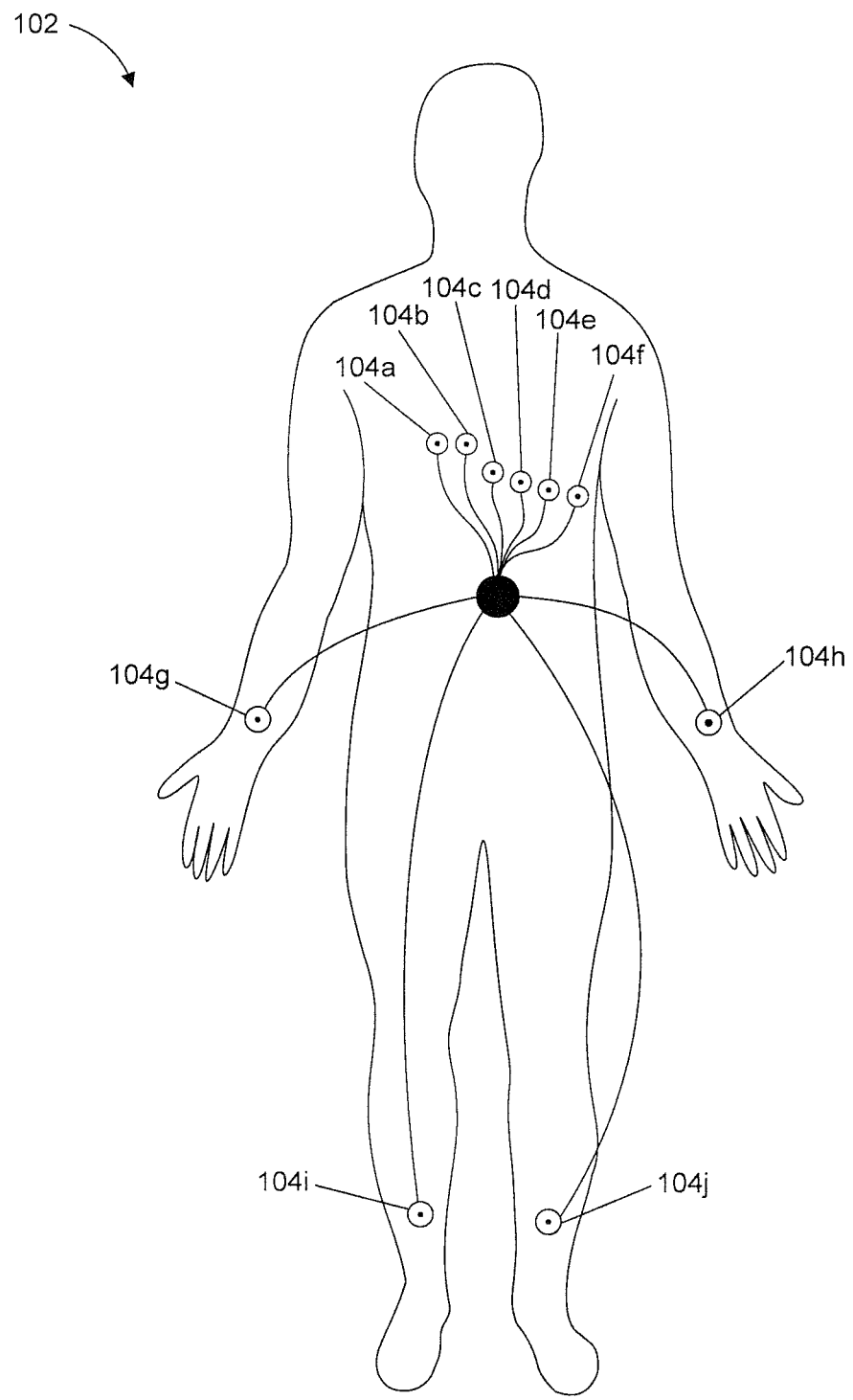
FIG. 1 illustrates leads of an ECG device placed on a patient, according to an embodiment.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 illustrates a patient 102 that is attached to various leads of an ECG recording device, according to an embodiment. The leads may be used to monitor a standard 12-lead ECG. In this example, six leads (leads 104a-f) may be placed across the chest of patient 102 while four other leads (leads 104g-j) are placed with two near the wrists and two near the ankles of patient 102.

It should be understood that the exact placement of the leads is not intended to be limiting. For example, the two lower leads 104i and 104j may be placed higher on the body, such as on the outer thighs. In another example, leads 104g and 104h are placed closer to the shoulders while leads 104i and 104j are placed closer to the hips of patient 102. In still other examples, not all ten leads are required to be used in order to monitor ECG signals from patient 102.

In an embodiment, signals are monitored from each of leads 104a-j during a standard 12-lead ECG recording. The resulting ECG signal may be analyzed over time to determine various health factors such as heart rate, strength of heart beat, and any indicators of abnormalities. However, changes in the various signals received amongst leads 104a-j may be very small and difficult to detect. Any trend in the changing signal amplitude for certain areas of the ECG morphology could be vital in predicting the onset of potentially fatal heart complications. For example, prediction of heart arrhythmias may be possible by observing trends in the R-wave heterogeneity, T-wave heterogeneity, P-wave heterogeneity and/or T-wave alternans from the monitored ECG signals. The observation of using T-wave alternans as a predictor for heart arrhythmias has been discussed previously in U.S. Pat. No. 6,169,919, the disclosure of which is incorporated by reference herein in its entirety. Spatial differences in ST-segment morphology, termed ST-segment heterogeneity, may provide evidence of regionality of myocardial ischemia, a characteristic that contributes to risk for lethal arrhythmia.

The challenge is to separate these biologically significant microvolt-level changes from the intrinsic differences in ECG morphology. In an embodiment, the technique employed herein utilizes a multi-lead ECG median-beat baseline for each lead, which allows for the determination of ECG residua by subtraction of the baseline from the collected ECG signals. These residua may be evaluated in association with R-wave and T-wave heterogeneity analysis and other parameters for heart arrhythmia prediction and/or for myocardial ischemia assessment. Ultimately, the implementation of embodiments described herein can lead to improved identification of individuals at risk for lethal cardiac arrhythmias and to a reduction in cases of sudden cardiac death.

Figure 2:
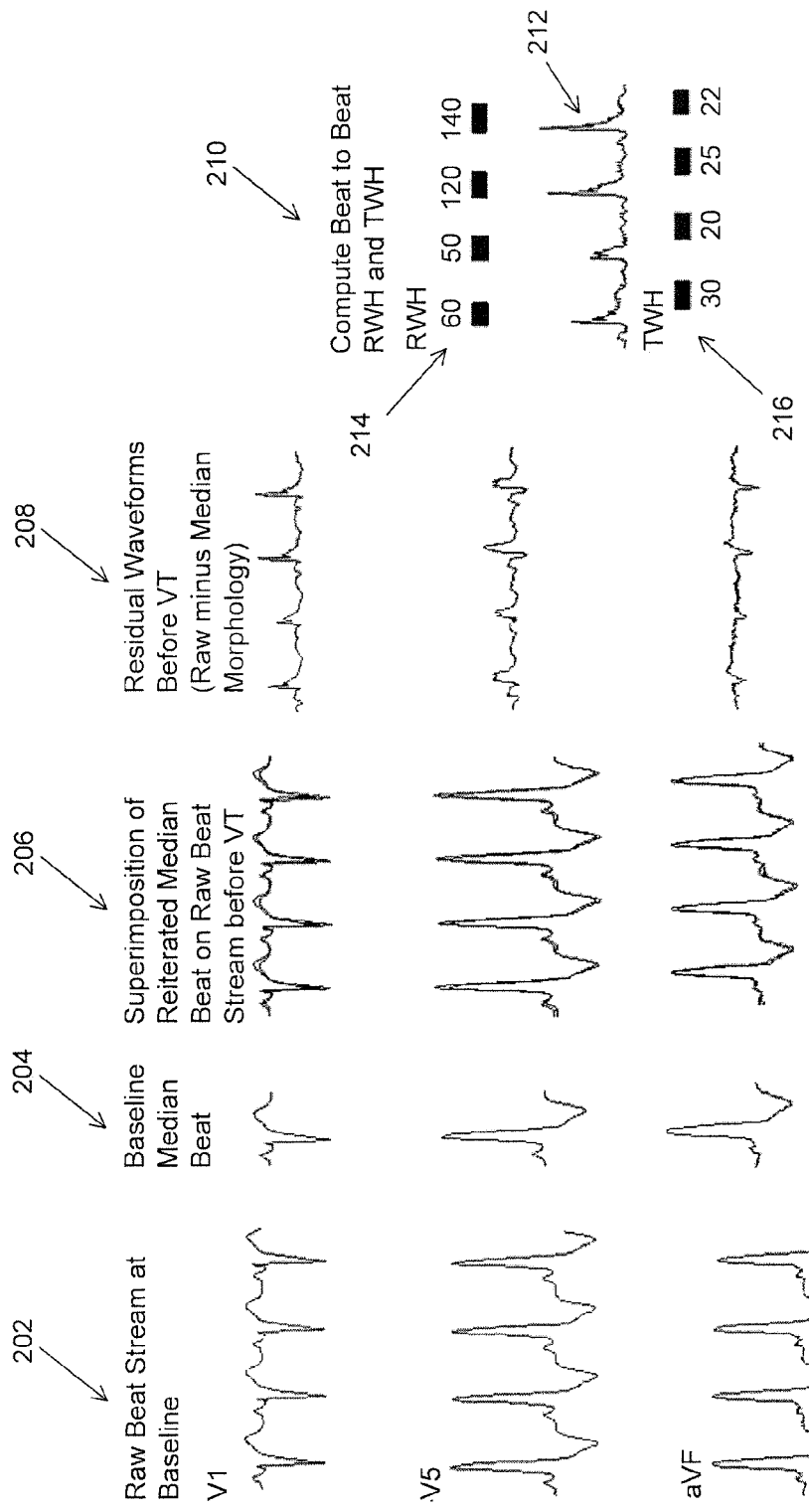
FIG. 2 illustrates signal processing techniques of an ECG signal, according to an embodiment.

FIG. 2 illustrates a signal processing procedure for generating ECG residua and detecting changes, for example, in R-wave and T-wave heterogeneity from the signals received from various leads, according to an embodiment. For simplicity, the signal processing procedure described with reference to FIG. 2 will be referred to herein as the multi-lead residuum procedure. In one example, signals from three different ECG leads (V1, V5, and aVF) are shown in column 202. The ECG signals to be analyzed in accordance with the present disclosure may be sensed in real-time from a patient and processed on a real-time or near real-time basis (e.g., within seconds or minutes of being collected from a patient). Alternatively, the ECG signals may be received from some storage medium (e.g., an analog or digital storage device) for analysis in accordance with the present disclosure.

A baseline recording 202 is generated from the signals received from each of the ECG leads, according to an embodiment. In one example, the baseline measurement is generated by computing a median-beat 204 from the collected signals shown in column 202. An example calculation of the median-beat $B_{i,n}(t)$ for n=1 . . . N beats, where i=1 . . . M ECG signals and M=all ECG leads, is shown below in equation 1.

$$B_{i,n}(t)=B_{i,n-1}(t)+\Delta_{i,n} \qquad (1)$$

$\Delta_{i,n}=-32$ if $\delta \leq -32$
$\Delta_{i,n}=\delta$ if $-1 \geq \delta \geq -32$
$\Delta_{i,n}=-1$ if $0 \geq \delta \geq -1$
$\Delta_{i,n}=0$ if $\delta=0$
$\Delta_{i,n}=1$ if $1 \geq \delta \geq 0$
$\Delta_{i,n}=\delta$ if $0 \geq \delta \geq 1$
$\Delta_{i,n}=32$ if $\delta \leq 32$
where $\delta=(ECG_{i,n-1}(t)-B_{i,n-1}(t))/8$
and $B_{i,0}(t)=ECG_{i,0}(t)$
i=1 . . . M ECG signals
n=1 . . . N Baseline Beats In an embodiment, the sequence starts with the first beat, and each successive beat then contributes a limited amount to the median-beat computation in each ECG lead. The baseline measurement contains nonpathologic morphologies in each ECG lead and may be associated with a period of quiet rest when morphology differences over time are at a minimum. This baseline measurement may be calculated by computing the median beat 204 over a time period between, for example, 5 and 10 minutes. Collection times over 10 minutes may be used as well, but would typically not be necessary for calculating a stable baseline signal. Alternatives to the use of median beats include calculating the baseline signal from an average of all the beats in the baseline time period or using a single, representative beat from the baseline time period as the baseline signal. These methods are simpler but not as robust as median beat calculation. Baseline measurements of the ECG signals received via leads V1, V5 , and aVF are shown in column 204.

Once the baseline measurement 204 has been generated, a second set of ECG recordings, $ECG_i(t)$, is made. In an embodiment, the second set of ECG recordings is made soon after (e.g., immediately after) the baseline recording. However, it is also possible that the second set of ECG recordings is made at any period of time after the baseline recording has been generated. For example, the baseline recording for a particular patient may be saved and used a year later when that patient returns to have a second set of ECG recordings made. It should also be understood that there is no restriction as to the duration of the second set of ECG recordings.

In an embodiment, the baseline measurement $B_{i,N}(t)$ and the second set of ECG recordings $ECG_i(t)$ for each lead are used to generate a residuum signal for each lead. In one example, each baseline measurement beat is reiterated and aligned either temporally or spatially with the various beats from the second ECG recordings for each lead in order to subtract the morphologies from one another (e.g., for a particular lead, the baseline measurement beat is subtracted from the various beats of the second ECG recording). In another example, each baseline measurement beat is reiterated and aligned either temporally or spatially with the various beats from the second ECG recordings for each lead, and the residuum signal for each lead is calculated as a quotient on a point by point basis where the numerator represents the second ECG recording and the denominator represents the baseline measurement. The residuum signal may represent a difference when subtracting, while the residuum signal may represent a fractional change when dividing.

Column 206 illustrates the superimposition of the baseline measurement 204 $B_{i,N}(t)$ over the second set of ECG recordings $ECG_i(t)$ in order to subtract the baseline signal, according to one embodiment. The residuum signal resulting from the subtraction for each lead is illustrated in column 208. Likewise, equation 2 below provides the generation of the residuum signal $e_i(t)$ when subtracting.

$$e_i(t)=ECG_i(t)-B_N(t) \qquad (2)$$

i=1 . . . M ECG signals
N=Number of beats in baseline sequence

According to another embodiment, a median beat is also calculated for the second set of ECG recordings, $ECG_i(t)$ to produce a second median beat for each lead. The median baseline beat for each lead may then be subtracted from the second median beat for each lead to generate a residuum signal for each lead. This could be done as an alternative to the superimposition of the baseline measurement 204 over the second set of ECG recordings, $ECG_i(t)$, illustrated in Column 206. In this alternate embodiment, the median baseline beat for each lead would be superimposed over the second median beat for each lead to generate the residuum signal for each lead.

Figure 11:
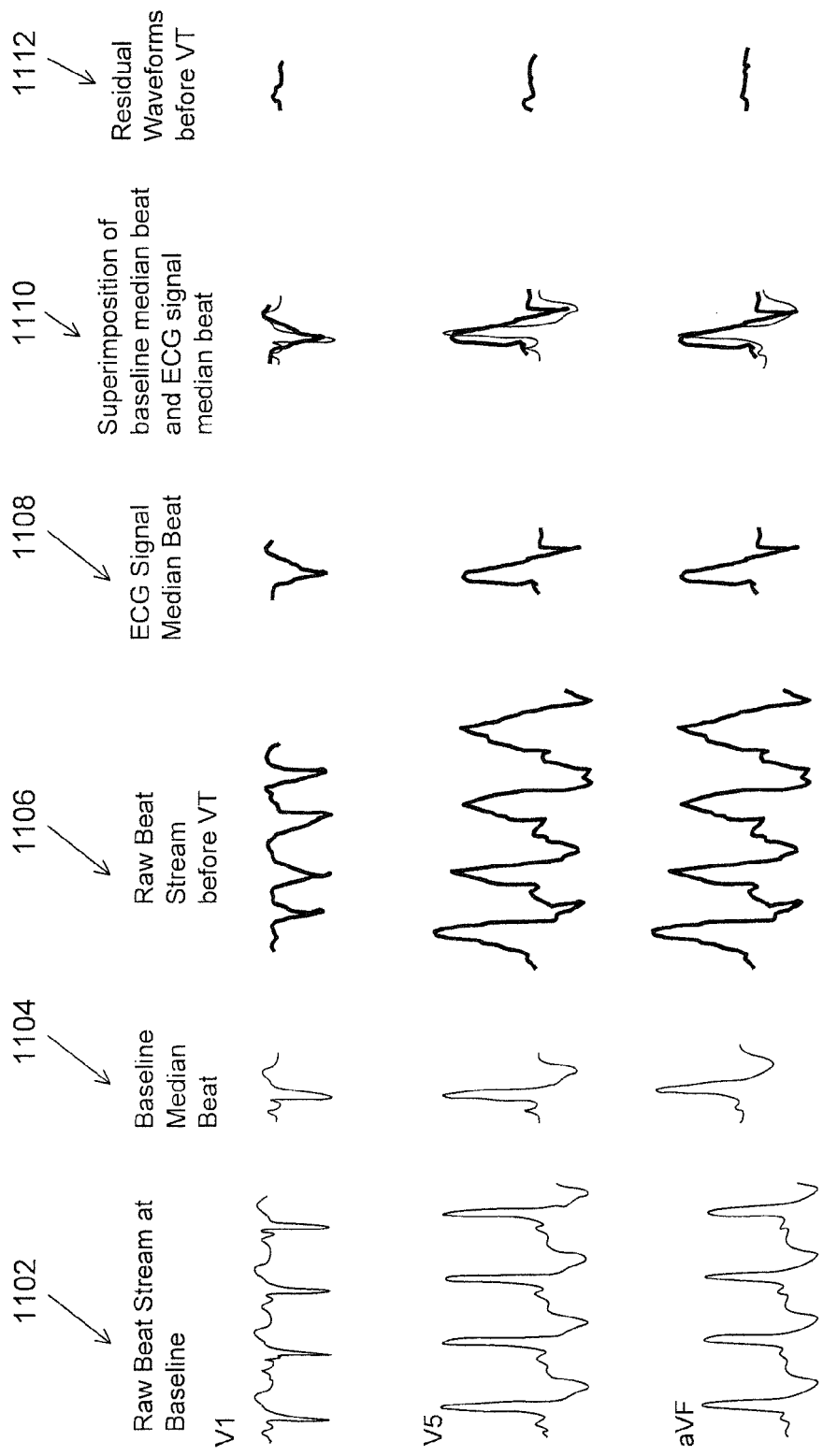
FIG. 11 illustrates signal processing techniques of an ECG signal, according to an embodiment.

An example of this embodiment using a second median beat for each lead is illustrated in FIG. 11. Many of the features in FIG. 11 are similar to those already discussed with reference to FIG. 2 above. For example, a baseline recording 1102 is generated from the signals received from each of the ECG leads V1, V5 , and aVF. A baseline median beat 1104 is calculated for each lead according to Equation 1 above. A second set of ECG signals are collected across the leads V1, V5 and aVF as illustrated in column 1106.

Column 1108 illustrates the generation of a median beat for the second set of ECG signals (i.e., a second median beat) for each lead, according to an embodiment. The calculation of this second median beat may be substantially similar to calculation of the baseline median beat illustrated in column 1104. For example, the amplitude of the second set of ECG signals as a function of time may be given by $S_{i,m}(t)$ for m=1 . . . M beats and i=1 . . . I ECG signals, where I=all ECG leads. The measurement signal $S_{i,m}(t)$ may be obtained, for example, from a 10 second ECG segment, or a short ECG segment during an exercise stress test or Holter recording. An example calculation of the ECG signal median-beat is shown below in equation 3.

$$S_{i,m}(t)=S_{i,m-1}(t)+\Delta_{i,m} \qquad (3)$$

$\Delta_{i,n}=-32$ if $\delta \leq -32$
$\Delta_{i,m}=\delta$ if $-1 \geq \delta \geq -32$
$\Delta_{i,m}=-1$ if $0 \geq \delta \geq -1$
$\Delta_{i,m}=0$ if $\delta=0$
$\Delta_{i,m}=1$ if $1 \geq \delta \geq 0$ $\Delta_{i,m} = 8$ if $0 \geq \delta \geq 1$
$\Delta_{i,m} = 32$ if $\delta \leq 32$
where $\delta = (ECG_{i,m-1}(t) - S_{i,m-1}(t))/8$
and $S_{i,0}(t) = ECG_{i,0}(t)$
i=1 . . . I ECG signals
m=1 . . . M Baseline Beats
t=−P . . . +R
where t=−P is the time of the P−Wave Onset
where t=0 is the time of the R−Wave Peak
where t=+R is the time of the T−Wave End Once both a baseline median beat and a second median beat have been calculated for each lead, the median beats may be superimposed so that R-waves are aligned. An example of this superimposition is illustrated in column 1110 of FIG. 11. In an embodiment, the baseline median beat is subtracted from the second median beat to generate a residuum signal for each lead as illustrated in column 1112. In another example, the residuum signal for each lead is calculated as a quotient on a point by point basis where the numerator represents the second median beat and the denominator represents the baseline median beat. Likewise, equation 4 below provides the generation of the residuum signal $e_i(t)$ when subtracting.

$$e_i(t) = S_{i,M}(t) - B_{i,N}(t) \quad (4)$$

i=1 . . . I ECG signals
N=Number of beats in Baseline sequence
M=Number of beats in Measurement sequence
t=−P . . . +R
where t=−P is the time of the P−Wave Onset
where t=0 is the time of the R−Wave Peak
where t=+R is the time of the T−Wave End Once the residuum signals have been calculated for each lead using any of the embodiments described above, they may be used for calculating the R-wave heterogeneity (RWH) and T-wave heterogeneity (TWH), according to an embodiment. By observing trends in the RWH and/or TWH, cardiac events such as ventricular tachycardia may be predicted well in advance, allowing for preventive procedures to be taken. The RWH and TWH may be calculated by first averaging the spatio-temporal signals of each of the residuum signals to generate an averaged residuum signal as shown below in equation 5.

$$\overline{e(t)} = \frac{1}{M} \sum_{i=1}^{M} e_i(t) \quad (5)$$

In the above equation, and for other equations used herein, M is an integer greater than two and equal to the number of total ECG signals collected. In one example, one ECG signal is recorded from each lead of the standard 12-lead ECG.

Next, in an embodiment, a second central moment 212 about the averaged residuum signal is determined by taking the mean-square deviation of the various ECG signals about the average signal. This step is shown below in Equation 6.

$$\mu_2(t) = \frac{1}{M} \sum_{i=1}^{M} (e_i(t) - \overline{e(t)})^2 \quad (6)$$

With the second central moment 212 calculated, RWH 214 may be determined as the maximum square root of the second central moment of the ECG residua occurring within the QRS segment. In an embodiment, the QRS segment begins at the Q-wave and ends at the J-point of a standard ECG signal. Equation 7 below provides an example calculation for the RWH.

$$RWH = \underset{Q\text{-}Waveonset \leq t \leq J\text{-point}}{MAX} \sqrt{\mu_2(t)} \quad (7)$$

TWH 216 may be determined as the maximum square root of the second central moment of the ECG residua occurring within the JT interval. The JT interval occurs approximately from 60 to 290 msec after the R-wave of a standard ECG signal. Equation 8 below provides an example calculation for the TWH.

$$TWH = \underset{J\text{-point} \leq t \leq T\text{-}waveend}{MAX} \sqrt{\mu_2(t)} \quad (8)$$

Computation of residuum signals may be also useful in calculating heterogeneity of the P-Wave (PWH) from its onset to offset, which relates to atrial arrhythmias, and heterogeneity of the ST-Segment (STWH) from the J-point to the onset of the T-wave, which identifies nonhomogeneous features of myocardial ischemia.

$$PWH = \underset{P\text{-}Waveonset \leq t \leq P\text{-}Waveoff}{MAX} \sqrt{\mu_2(t)} \quad (9)$$

$$STWH = \underset{J\text{-point} \leq t \leq T\text{-}Waveonset}{MAX} \sqrt{\mu_2(t)} \quad (10)$$

Column 210 illustrates results 212 of second central moment analysis of the residuum signals as well as the areas of the signal that correspond to RWH measurements 214 and TWH measurements 216, according to an embodiment. As shown in the example, the RWH and TWH measurements may change between beats. Peak levels of RWH and TWH are averaged for each 15-sec sampling period. Trends in the changing RWH and/or TWH may be used to identify short- or long-term risk for cardiac arrhythmias. In one example, the RWH and/or TWH may be reported over a given period of time for further analysis and/or data presentation.

Using both the baseline median beat and second median beat in the calculation of a residuum signal for each lead allows for high-throughput analysis of a plurality of patients. In one example study, over 5600 patient ECGs from a database were analyzed with a processing time of a few seconds per patient to yield highly predictive results in terms of assessing cardiovascular mortality and sudden cardiac death (SCD). The patients (5618 adults, 46% men; age 50.9±12.5 years), were enrolled in the Health 2000 Study, an epidemiological survey representative of the entire Finnish adult population. During follow-up of 7.7±1.4 years, a total of 72 SCDs occurred. Increased RWH, JWH and TWH in left precordial leads (V4-V6) were univariately associated with SCD (P<0.001, each). When adjusted with clinical risk markers, JWH and TWH remained independent predictors of SCD. Increased TWH (≥102 µV) was associated with a 1.7-fold adjusted relative risk (95% confidence interval [CI]: 1.0-2.9; P=0.048) and increased JWH (≥123 µV) with a 2.0-fold adjusted relative risk for SCD (95% CI: 1.2-3.3;

P=0.006). When both TWH and JWH were above threshold, the adjusted relative risk for SCD was 2.9-fold (95% CI: 1.5-5.7; P=0.002). When all heterogeneity measures (RWH, JWH and TWH) were above threshold, the risk for SCD was 3.3-fold (95% CI: 1.4-8.0; P=0.009).

Figure 3:
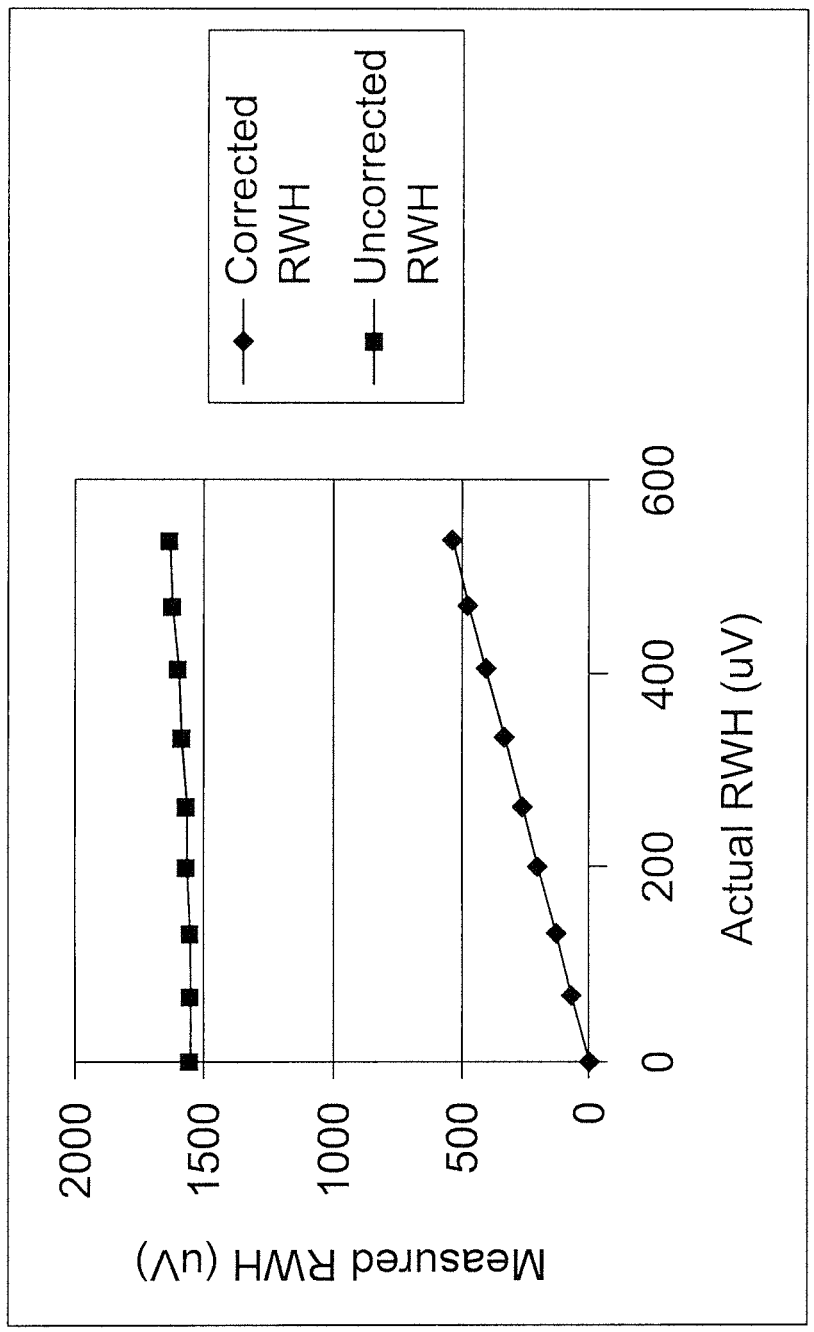
FIG. 3 illustrates results of calculating R-wave heterogeneity in simulated ECGs, according to an embodiment.

FIG. 3 illustrates results for measuring RWH in simulated ECG signals with various RWH levels. The ECG signals were generated using a C++ program with P-waves, R-waves, T-waves, and ST segments approximated by geometric shapes whose relative timing and amplitude were similar to surface ECGs. The results in FIG. 3 demonstrate that the measured RWH (y-axis) was highly correlated with the actual input RWH (x-axis) when corrected by using the multi-lead residuum procedure (diamonds). However, when uncorrected, the program was unable to determine accurately the RWH as shown by the uncorrected data points (squares), as results varied by up to 1500 microvolts from the input RWH signal.

Figure 4:
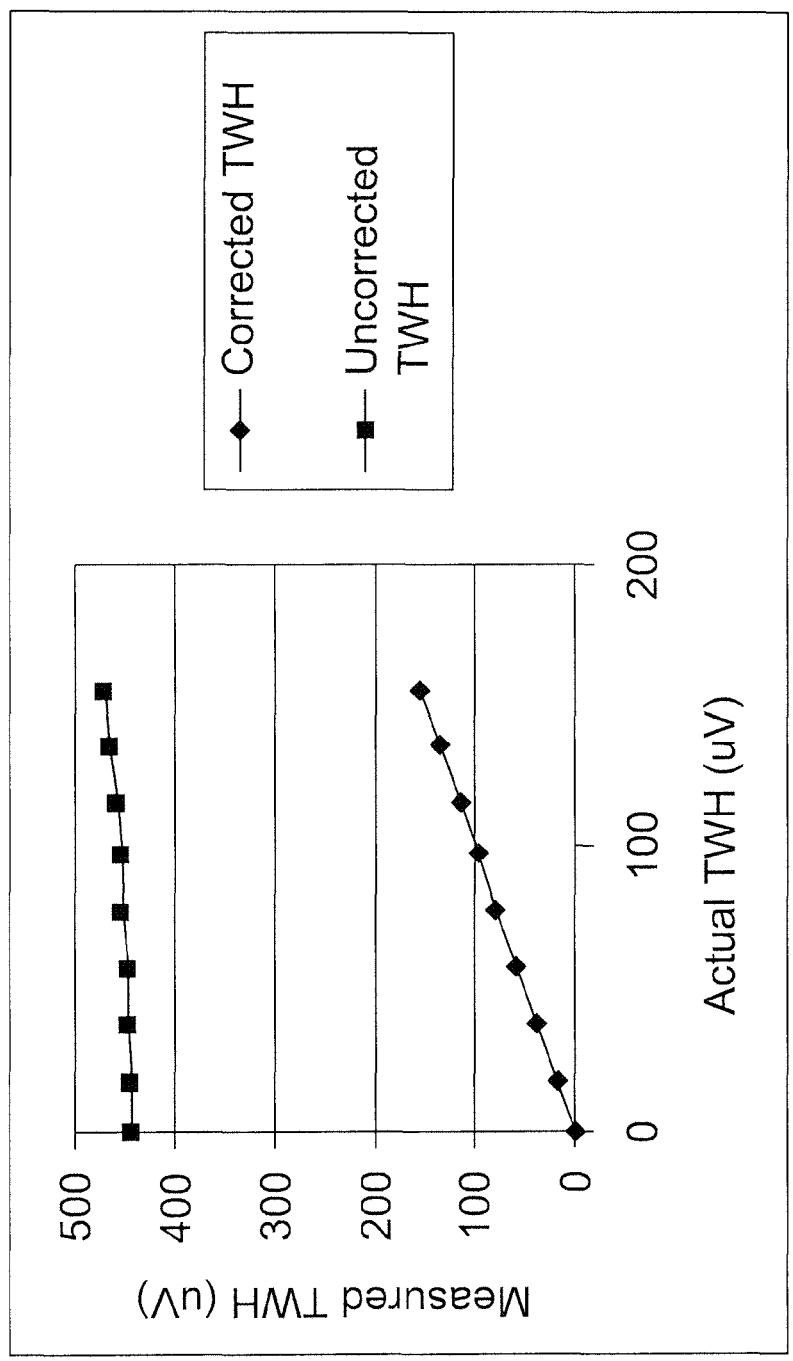
FIG. 4 illustrates results of calculating T-wave heterogeneity in simulated ECGs, according to an embodiment.

FIG. 4 illustrates results for measuring TWH in simulated ECG signals with various TWH levels. The ECG signals were generated using a C++ program with P-waves, R-waves, T-waves, and ST segments approximated by geometric shapes whose relative timing and amplitude were similar to surface ECGs. The results in FIG. 4 demonstrate that the measured TWII (y-axis) was highly correlated with the actual input TWH (x-axis) when corrected by using the multi-lead residuum procedure (diamonds). However, when uncorrected, the program was unable to determine accurately the TWH as shown by the uncorrected data points (squares), as results varied by up to 450 microvolts from the input TWH signal.

Thus, the RWH and TWH algorithm accurately tracked heterogeneities in R-wave and T-wave morphology in simulated ECGs when using the multi-lead residuum procedure but not in its absence. When calculating the residua, a linear relationship between the input and output values of RWH (range: 0-538 µV) and TWH (0-156 µV) estimated by second central moment analysis with a correlation coefficient of $r^2$=0.999 (P<0.001) was observed.

The embodied multi-lead residuum procedure for accurately determining RWH and TWH was validated via the simulation experiments shown in FIGS. 3 and 4. However, analysis of ECGs from a clinical trial was also conducted to demonstrate the capacity of the procedure to predict dangerous cardiac complications such as ventricular tachycardia.

The capacity of multi-lead ECG residua to predict ventricular arrhythmia was examined by comparing RWH and TWH output with and without calculation of the residua in clinical ambulatory ECG recordings obtained in hospitalized patients with non-sustained ventricular tachycardia. The PRECEDENT (Prospective Randomized Evaluation of Cardiac Ectopy with Dobutamine or Nesiritide Therapy) trial (www.clinicaltrials.org #NCT00270400) enrolled 255 patients aged ≥18 years with NYHA class III or IV congestive heart failure and symptomatic, decompensated congestive heart failure for which inpatient, single-agent, intravenous therapy with either nesiritide or dobutamine was deemed appropriate. All patients were monitored by ambulatory ECG recording for the 24-hour period immediately before the start of the study drug (pre-randomization ambulatory ECG tape).

Ambulatory ECGs recorded during the pre-randomization phase of the PRECEDENT trial were analyzed from all 22 patients who experienced a single bout of ventricular tachycardia (≥4 beats at heart rates of >100 beats/min) following 120 minutes of stable sinus rhythm and without atrial fibrillation. The Beth Israel Deaconess Medical Center Committee on Clinical Investigations certified the exempt status of this reanalysis of existing data from a completed clinical trial under exemption number 4 of the Code of Federal Regulations, 45 CFR 46.101(b).

The continuous ECGs were analyzed with and without correction by ECG residua in leads V1, V5 , and aVF by subtracting the median-beat baseline ECG, which was generated from ECGs recorded during a quiescent period at 60 to 75 minutes before the arrhythmia occurred. Then, the ECG heterogeneity signal was computed from the ECG residua as the square root of the sum of the squares of the differences between the corrected signal and the mean of the corrected signals. RWH was calculated as the maximum value of the heterogeneity signal in the interval from the beginning of the Q wave to the end of the S wave. TWH was calculated as the maximum value of the heterogeneity signal in the interval between the J point and the end of the T wave. The analysis window began at 75 minutes before ventricular tachycardia. RWH and TWH maxima were computed for each 15-second interval, comparing signals in leads V1, V5, and aVF, and averaged over 15-minute epochs. Correlation coefficients of input-output relationships were calculated for input-output relationships by Pearson's coefficient. RWH and TWH levels at 45-60, 30-45, 15-30, and 0-15 minutes were compared with baseline at 60 to 75 minutes before the onset of the arrhythmia in PRECEDENT trial patients. ANOVA was used with Tukey test for multiple comparisons (*p<0.05).

Figure 5:
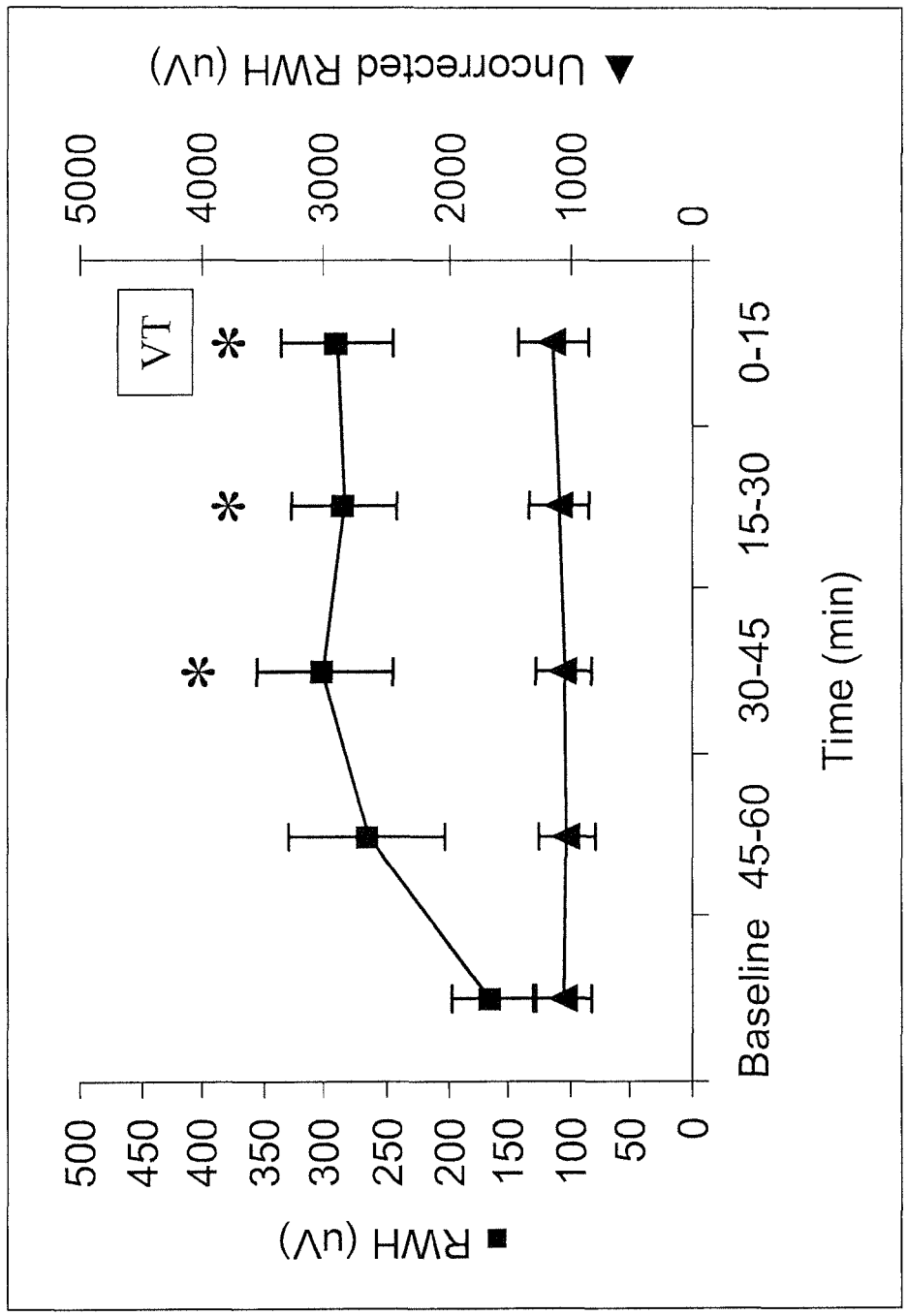
FIG. 5 illustrates results of measured R-wave heterogeneity before a ventricular tachycardia event, according to an embodiment.
Figure 6:
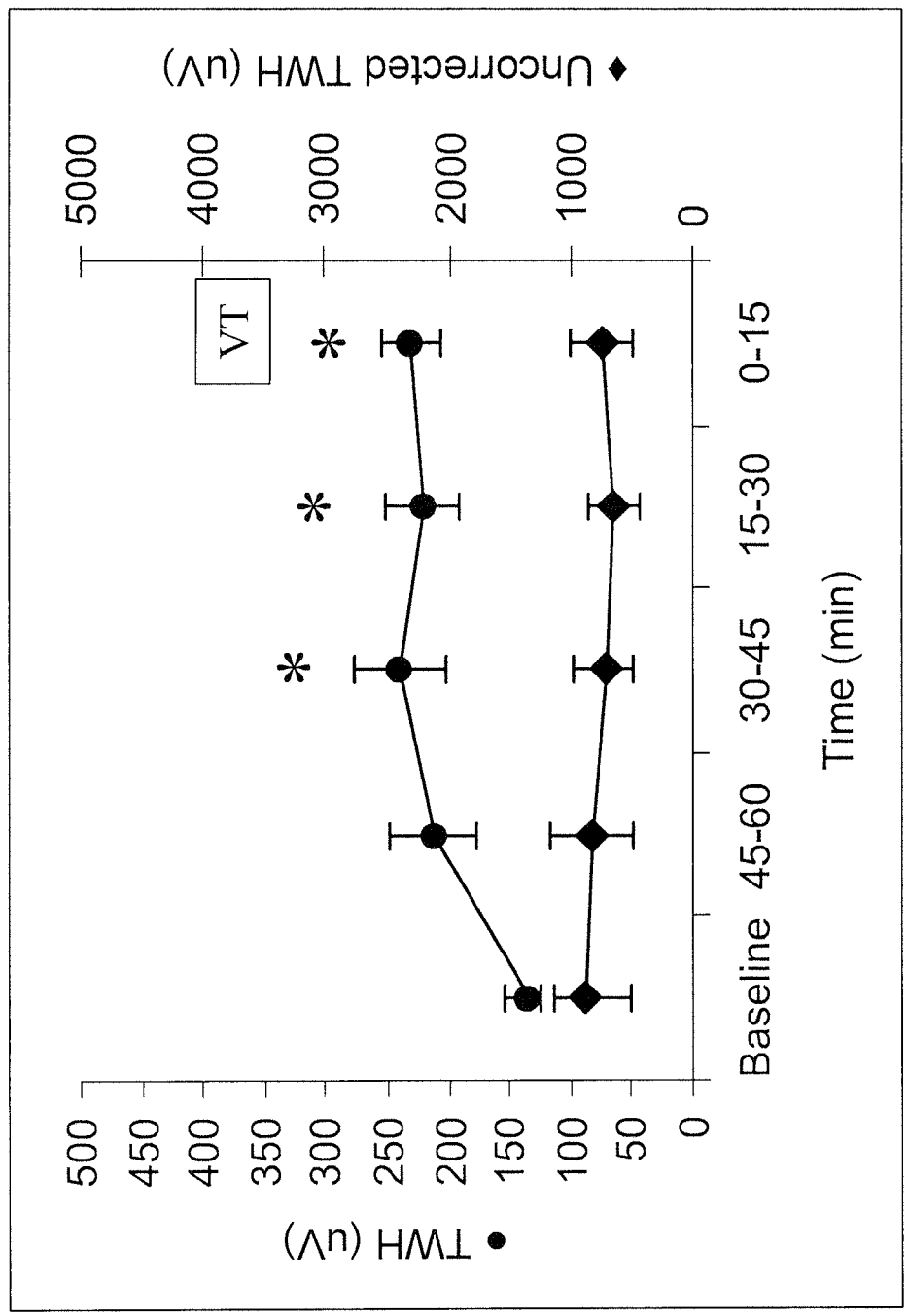
FIG. 6 illustrates results of measured T-wave heterogeneity before a ventricular tachycardia event, according to an embodiment.

FIGS. 5 and 6 illustrate the results for the RWH and TWH respectively obtained for those patients prior to ventricular tachycardia. A noticeable crescendo in RWH (FIG. 5) and TWH levels (FIG. 6) was observed prior to ventricular tachycardia when using the multi-lead residuum procedure (left y-axes). Maximum RWH across leads V1, V5, and aVF rose from 164.1±33.1 µV at baseline to 299.8±54.5 ρV at 30 to 45 minutes before the arrhythmia (P<0.05). Meanwhile, maximum TWH across leads V1, V5, and aVF rose from 134.5±20.6 µV at baseline to 239.2±37.0 µV at 30 to 45 minutes before the arrhythmia (p<0.05). Just before ventricular tachycardia, maximum RWH and TWH levels remained elevated at 289.5±45.9 and 230.9±24.7 µV, respectively (p<0.05). Although the extent of change varied among patients, the crescendo pattern in ECG heterogeneity before non-sustained ventricular tachycardia was consistent (Pearson correlation coefficient comparing RWH and TWH, 0.51; P=0.01). In 20 of 22 (91%) patients, RWH or TWH remained elevated before onset of non-sustained ventricular tachycardia.

When R-wave and T-wave heterogeneity were calculated without employing the multi-lead residuum procedure, the levels of both RWH (FIG. 5) and TWH (FIG. 6) were high during the initial baseline period (right y-axes). The values were 1061.0±222.9 µV for RWH and 882.5±375.2 µV for TWH and were not statistically different at the time of onset of ventricular tachycardia.

Figure 7:
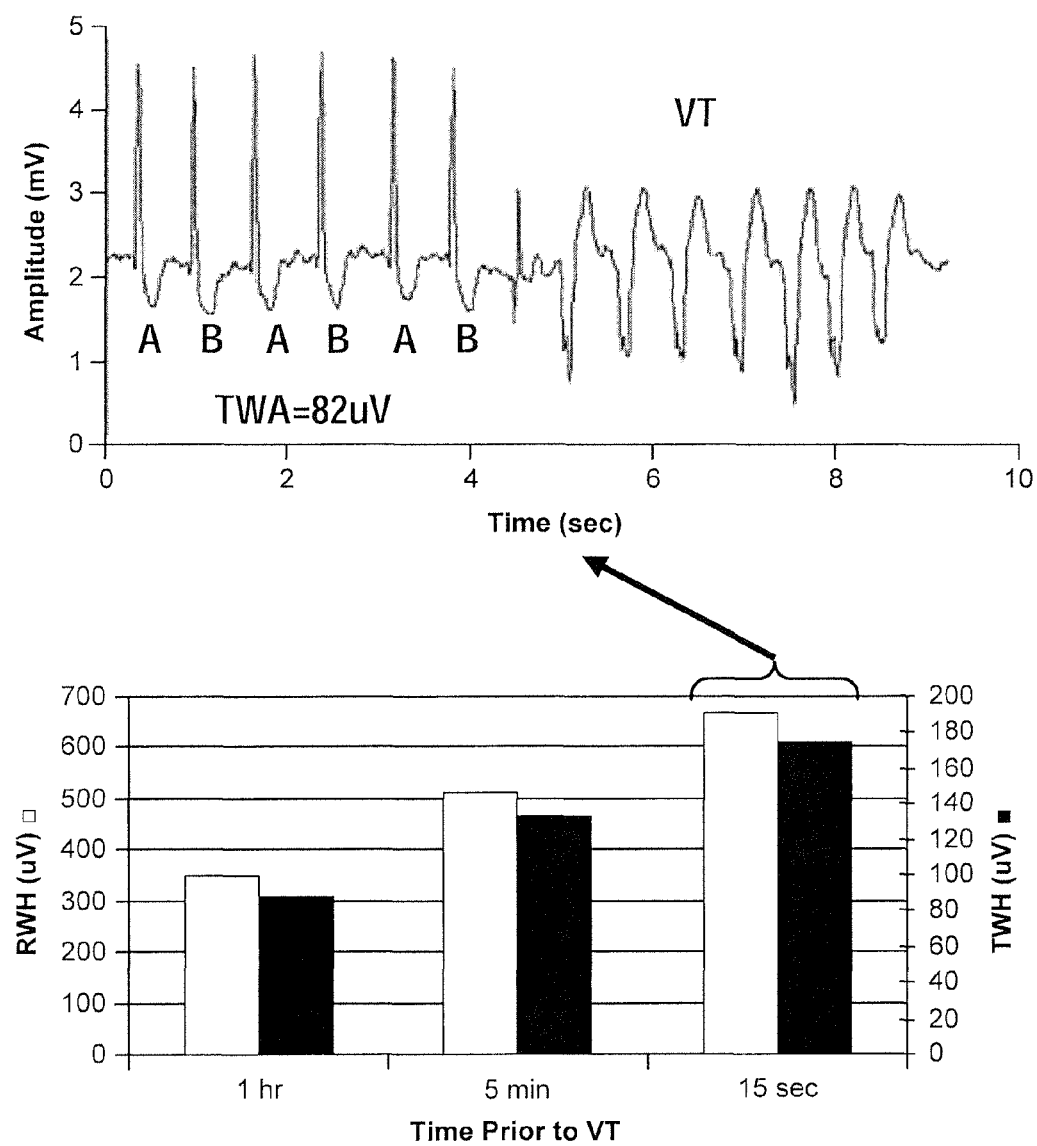
FIG. 7 illustrates results of measured R-wave and T-wave heterogeneity before a ventricular tachycardia event, according to an embodiment.

T-wave alternans (TWA) is another indicator of risk for lethal cardiac arrhythmias and can also be measured from the ECG along with the TWH measurements, according to an embodiment. FIG. 7 (lower panel) provides an example of the measured TWH (right y-axis) and RWH (left y-axis) of one patient at various times before the patient experienced ventricular tachycardia. Also illustrated is the measured TWA (~82 V) (upper panel) during the time leading up to the ventricular tachycardia. This patient exhibited increased levels of RWH and TWH that heralded the onset of TWA and ventricular tachycardia.

As mentioned previously, PWH reflects the depolarization phase of the atria. An intra-cardiac lead may be used to measure both atrial depolarization and repolarization heterogeneity more accurately. The latter reflects the repolarization phase of the atria. Typically, the repolarization phase of the atria is difficult to detect using surface leads as it is masked by the large R-wave deflection, which reflects ventricular depolarization. The intra-cardiac lead is less susceptible to noise and is capable of measuring the atrial repolarization heterogeneity. In an embodiment, both the repolarization and depolarization phases of the atria are used to determine the full atrial ECG heterogeneity.

Figure 8:
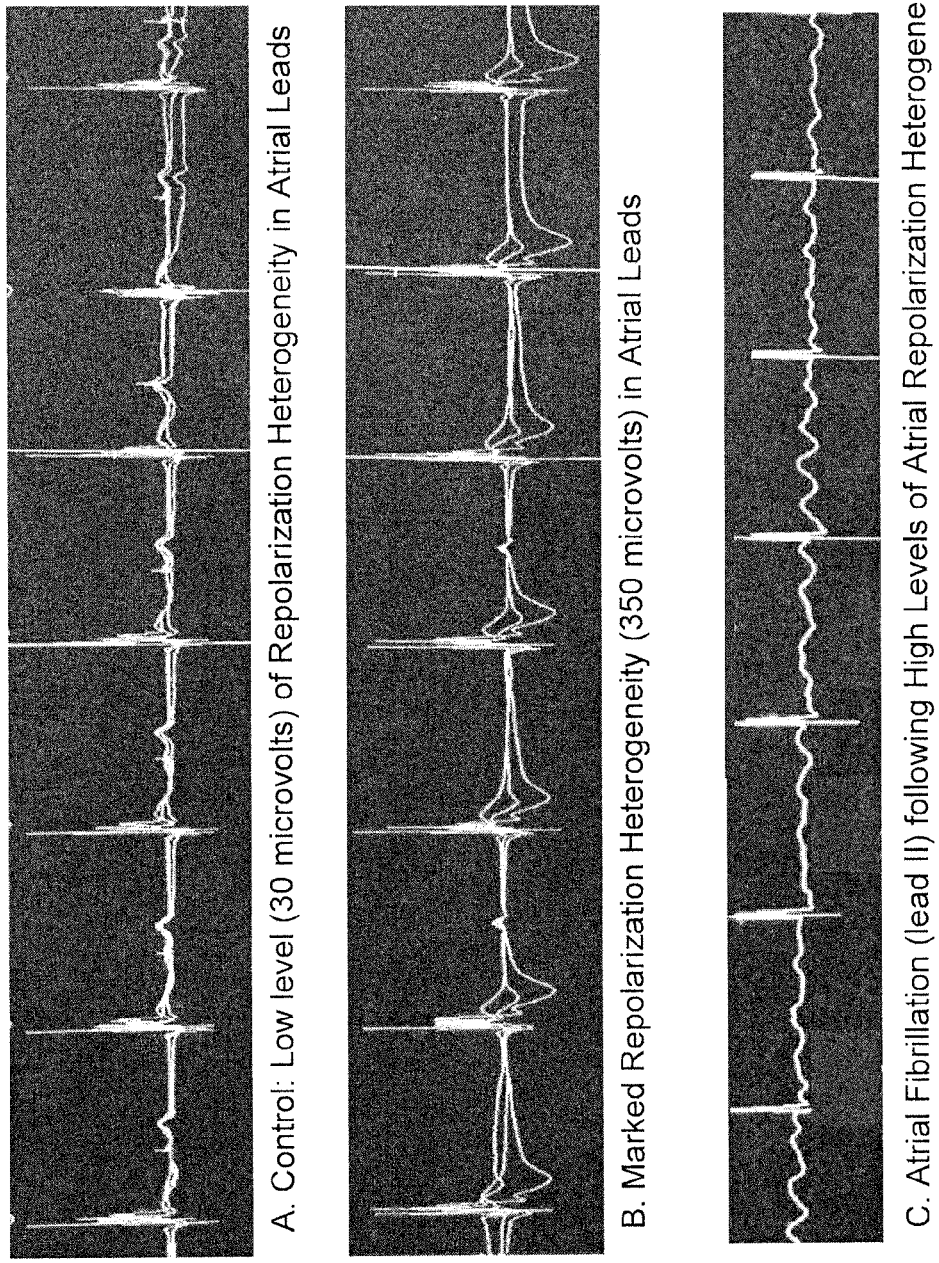
FIG. 8 illustrates results of measured atrial ECG heterogeneity before onset of atrial fibrillation, according to an embodiment.

FIG. 8 illustrates results of measured atrial ECG heterogeneity before onset of atrial fibrillation, according to an embodiment. The recordings are of atrial ECGs prior to and during vagus nerve stimulation in a porcine model. This procedure replicates a condition of heightened vagus nerve activity, which is an important factor known to predispose to atrial fibrillation in patients. Prior to vagus nerve stimulation (panel A), ECG signals recorded from three pairs of electrodes on an intra-cardiac catheter show that the waveforms are relatively superimposable. In another embodiment, as few as two pairs of electrodes on an intra-cardiac catheter may be used to record the atrial ECGs. During vagus nerve stimulation (panel B), there is a marked splay in the repolarization phase of the atrial ECG. Shortly thereafter (panel C), atrial fibrillation developed, as indicated by a chaotic, irregular pattern in the isoelectric phase between the distinct R-wave spikes in the ECG.

Figure 9:
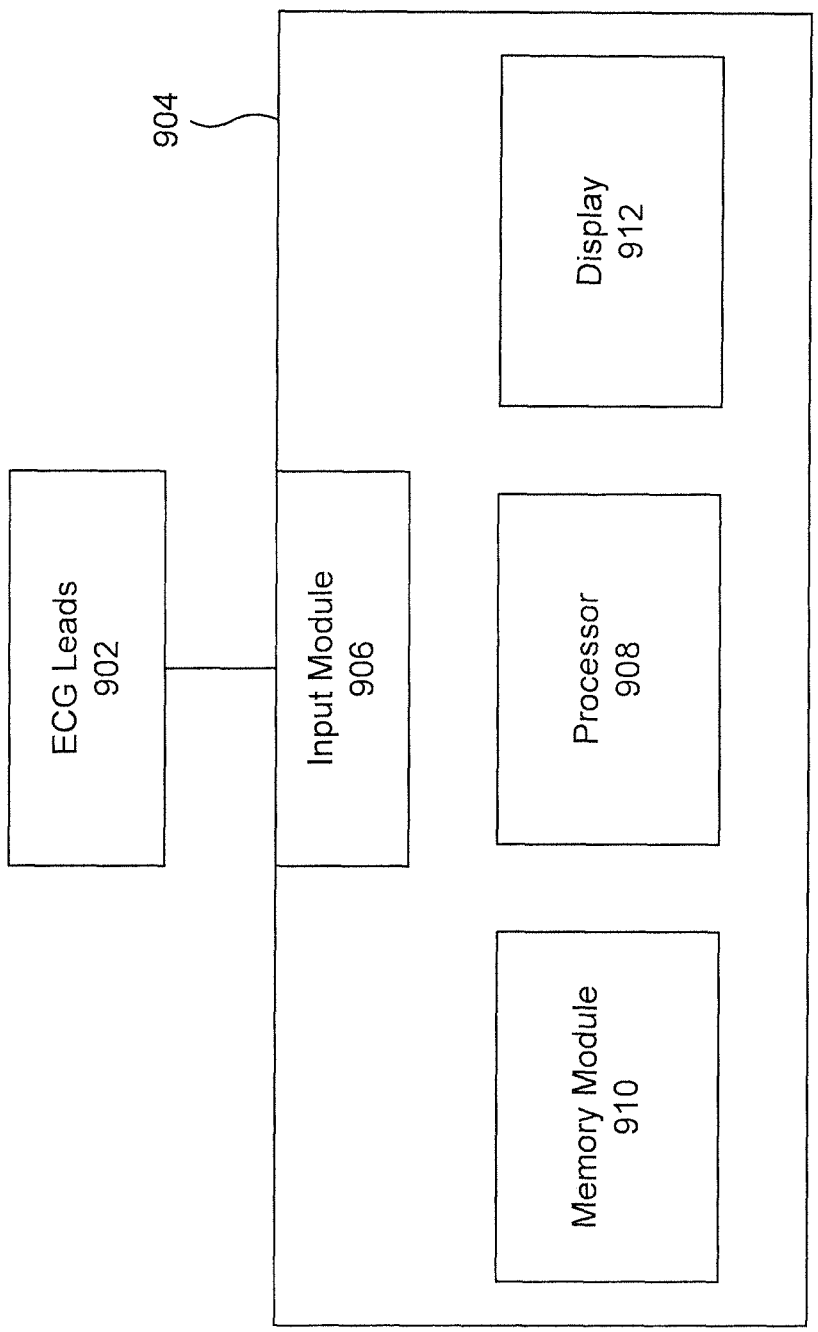
FIG. 9 illustrates an example ECG system, according to an embodiment.

FIG. 9 illustrates an example ECG system 900 configured to perform the embodied multi-lead residuum procedure. ECG system 900 may be used at a hospital or may be a portable device for use wherever the patient may be. In another example, ECG system 900 may be an implantable biomedical device with leads implanted in various locations around the body of a patient. ECG system 900 may be part of or may be coupled with other implantable biomedical devices such as a cardiac pacemaker, an implantable cardioverter-defibrillator (ICD) or a cardiac resynchronization therapy (CRT) device. In the case of ICD or CRT devices, analysis of the residuum signal will be analyzed after inverse filtering of the ECG signal to offset device-specific ECG filters and reconstruct the device output.

ECG system 900 includes leads 902 and a main unit 904. Leads 902 may comprise any number and type of electrical lead. For example, leads 902 may comprise ten leads to be used with a standard 12-lead ECG. Leads 902 may be similar to leads 104a-j as illustrated in FIG. 1 and described previously. In another example, leads 902 may comprise implanted electrical leads, such as insulated wires placed throughout the body.

Main unit 904 may include an input module 906, a processor 908, a memory module 910 and a display 912. Input module 906 includes suitable circuitry and hardware to receive the signals from leads 902. As such, input module 906 may include components such as, for example, analog-to-digital converters, de-serializers, filters, and amplifiers. These various components may be implemented to condition the received signals to a more suitable form for further signal processing to be performed by processor 908.

It should be understood that in the case of the embodiment where ECG system 900 is an implantable biomedical device, display 912 may be replaced with a transceiver module configured to send and receive signals such as radio frequency (RF), optical, inductively coupled, or magnetic signals. In one example, these signals may be received by an external display for providing visual data related to measurements performed by ECG system 900 and analysis performed after inverse filtering of the received signal to reconstruct the signal following filtering by the device.

Processor 908 may include one or more hardware microprocessor units. In an embodiment, processor 908 is configured to perform signal processing procedures on the signals received via input module 906. For example, processor 908 may perform the multi-lead residuum procedure as previously described for aiding in the prediction of heart arrhythmias. Processor 908 may also comprise a field-programmable gate array (FPGA) that includes configurable logic. The configurable logic may be programmed to perform the multi-lead residuum procedure using configuration code stored in memory module 910. Likewise, processor 908 may be programmed via instructions stored in memory module 910.

Memory module 910 may include any type of memory including random access memory (RAM), read-only memory (ROM), electrically-erasable programmable read-only memory (EEPROM), FLASH memory, etc. Furthermore, memory module 910 may include both volatile and non-volatile memory. For example, memory module 910 may contain a set of coded instructions in non-volatile memory for programming processor 908. The calculated baseline signal may also be stored in either the volatile or non-volatile memory depending on how long it is intended to be maintained. Memory module 910 may also be used to save data related to the calculated TWH or RWH, including trend data for each.

Figure 10:
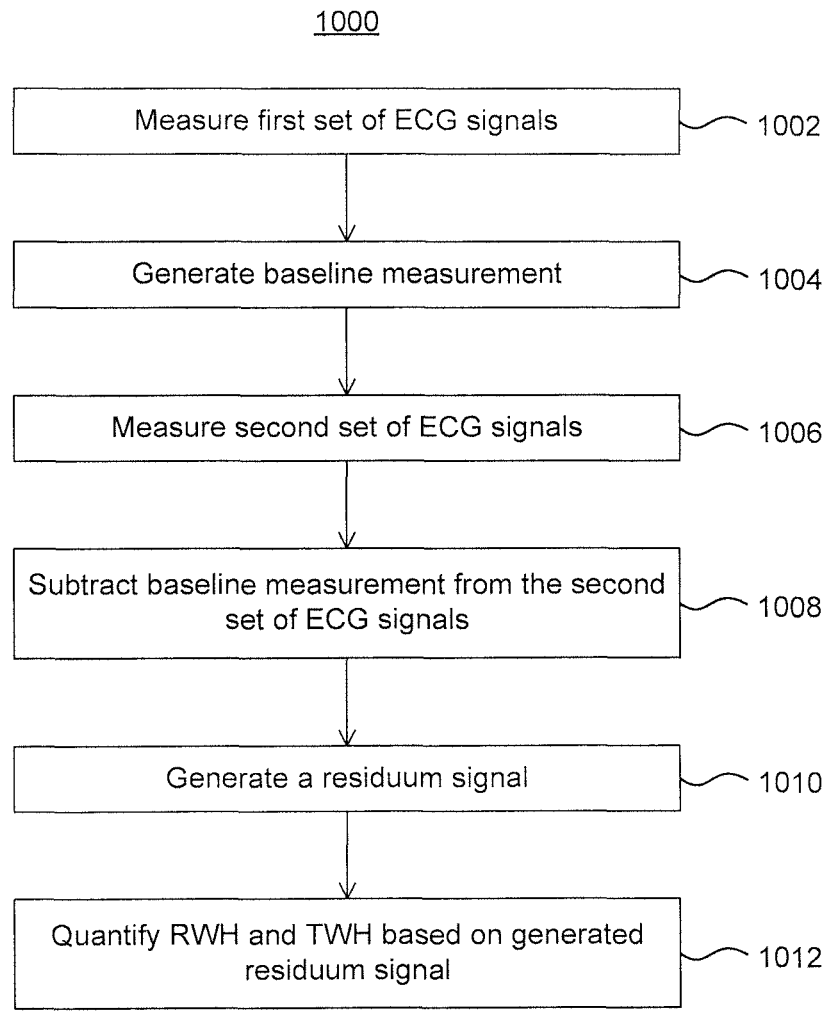
FIG. 10 illustrates an example method, according to an embodiment.

In an embodiment, main unit 904 includes display 912 for providing a visual representation of the received signals from leads 902. Display 912 may utilize any of a number of different display technologies such as, for example, liquid crystal display (LCD), light emitting diode (LED), plasma or cathode ray tube (CRT). An ECG signal from each of leads 902 may be displayed simultaneously on display 912. In another example, a user may select which ECG signals to display via a user interface associated with main unit 904. Display 912 may also be used to show data trends over time, such as displaying trends of the calculated RWH and TWH FIG. 10 illustrates a flowchart depicting a method 1000 for predicting heart arrhythmias based on RWH and TWH, according to an embodiment. Method 1000 may be performed by the various components of ECG system 900. It is to be appreciated that method 1000 may not include all operations shown or perform the operations in the order shown.

Method 1000 begins at step 1002 where a first set of ECG signals is monitored from a patient. The signals may be monitored via leads such as those illustrated in FIG. 1, or via implantable leads.

At step 1004, a baseline measurement associated with the morphology of the measured first set of ECG signals is generated. The baseline measurement may be generated by computing a median-beat sequence as described previously. The baseline measurement may be calculated, for example, over a period of 5 to 10 minutes in order to achieve a stable baseline signal. In an embodiment, a baseline measurement is generated for each lead of the standard 12-lead ECG.

At step 1006, a second set of ECG signals is monitored from the patient. The second set of signals may be monitored directly after monitoring the first set of signals or at any time after monitoring the first set of signals.

At step 1008, the baseline measurement is subtracted from the second set of monitored ECG signals, according to an embodiment. Each baseline measurement beat may be lined up either temporally or spatially with the various beats from each collected ECG signal for each lead in order to subtract the morphologies from one another. In another embodiment, the second set of monitored ECG signals may be divided by the baseline measurement on a point-by-point basis. Step 1008 may be performed independently for each lead of the standard 12-lead ECG using the baseline signal generated for each associated lead.

At step 1010, a residuum signal is generated for each lead based on the operation performed in step 1008 (e.g., subtraction or division according to the example embodiments described above). The residuum signal may be used to identify microvolt-level signal changes in particular segments of the ECG signal that would be otherwise difficult to detect.

At step 1012, RWH and TWH are quantified based on the generated residuum signals. In an embodiment, the residuum signals are calculated from each lead and the second central moment is derived for determining RWH and TWH.

Figure 12:
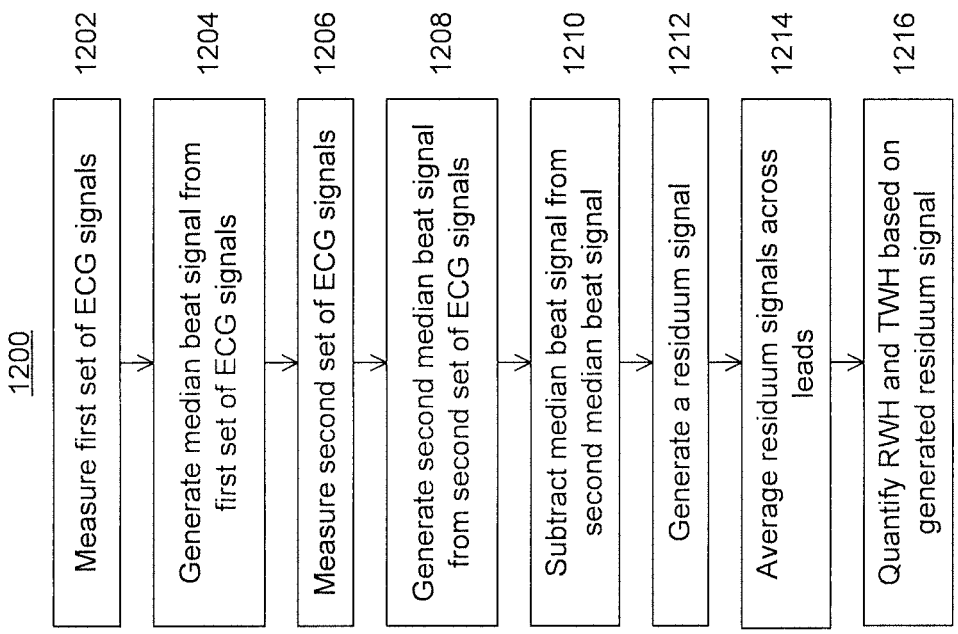
FIG. 12 illustrates an example method, according to an embodiment.

FIG. 12 illustrates a flowchart depicting another method 1200 for predicting heart arrhythmias based on RWH and TWH, according to an embodiment. Method 1200 may be performed by the various components of ECG system 900. It is to be appreciated that method 1200 may not include all operations shown or perform the operations in the order shown. Method 1200 enables high-throughput analysis of patient ECGs for determining arrhythmia risk.

Method 1200 begins at step 1202 where a first set of ECG signals is monitored from a patient. The signals may be monitored, for example, via external leads such as those illustrated in FIG. 1 or via implantable leads in various configurations or combinations.

At step 1204, a baseline measurement associated with the morphology of the measured first set of ECG signals is generated. The baseline measurement may be generated by computing a median-beat sequence as described previously. The baseline measurement may be calculated, for example, over a period of 5 to 10 minutes in order to achieve a stable baseline median beat signal. In an embodiment, a baseline measurement is generated for each lead of the standard 12-lead ECG. The baseline measurement may include only a single median beat.

At step 1206, a second set of ECG signals is monitored from the patient. The second set of signals may be monitored directly after monitoring the first set of signals or at any time after monitoring the first set of signals.

At step 1208, a median beat associated with the morphology of each ECG signal of the second set of ECG signals (i.e., a second median beat for each second ECG signal) is generated. A different second median beat may be calculated for each lead used to collect the second set of ECG signals. The median beat may be calculated, for example, over a period of 10 seconds.

At step 1210, the baseline median beat for each lead is subtracted from the second median beat for each lead of the second set of ECG signals. Each baseline median beat may be lined up either temporally or spatially with each second median beat of the second set of ECG signals in order to subtract the morphologies from one another.

At step 1212, a residuum signal is generated for each lead based on the subtraction performed in step 1210. The residuum signal may be used to identify microvolt-level signal changes in particular segments of the ECG signal that would be otherwise difficult to detect.

At step 1214, the residuum signals are averaged across each of the leads to generate an average residuum signal.

At step 1216, RWH and TWH are quantified based on the generated residuum signals and the average residuum signal.

In an embodiment, the residuum signals are calculated from each lead and the second central moment is derived for determining RWH and TWH.

Either of methods 1000 or 1200 may be realized as a computer program product stored on a computer readable media. The computer program product includes a set of instructions that, when executed by a computing device, such as processor 908, perform the series of steps illustrated as part of either method 1000 or method 1200. Additionally, the instructions may include operations for measuring T-wave alternans (TWA) and determining trends of peak TWA, TWH and RWH values. The trends may be used to predict the onset of various heart arrhythmias, such as ventricular tachycardia.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of quantifying risk of cardiac arrhythmia, comprising:
   receiving a first set of electrocardiogram (ECG) signals from spatially separated leads;
   generating, for each ECG signal in the first set of ECG signals, a median beat associated with the morphology of each respective ECG signal of the first set of ECG signals;
   receiving a second set of ECG signals from spatially separated leads;
   generating, for each ECG signal in the second set of ECG signals, a second median beat associated with the morphology of each respective ECG signal of the second set of ECG signals, wherein each second median beat corresponds to a respective one of the first median beats;

calculating, for each ECG signal in the first set of ECG signals and a corresponding ECG signal in the second set of ECG signals, a residuum signal based on the first median beat for each ECG signal in the first set of ECG signals and the corresponding second median beat for each ECG signal in the second set of ECG signals;

averaging the residuum signals to produce an averaged residuum signal; and quantifying a spatio-temporal heterogeneity of the second set of ECG signals based on the residuum signals and the averaged residuum signal, wherein the spatio-temporal heterogeneity is associated with arrhythmia risk.

2. The method of claim 1, wherein the quantifying step comprises:

quantifying at least one of R-wave heterogeneity, T-wave heterogeneity, P-wave heterogeneity, and ST-segment heterogeneity.

3. The method of claim 2, further comprising identifying a peak level of at least one of quantified R-wave heterogeneity, T-wave heterogeneity, P-wave heterogeneity, and ST-segment heterogeneity.

4. The method of claim 3, further comprising determining a trend of at least one of peak R-wave heterogeneity level, peak T-wave heterogeneity level, peak P-wave heterogeneity level, and peak ST-segment heterogeneity level over a period of time.

5. The method of claim 3, wherein the step of identifying further comprises using the at least one of peak R-wave heterogeneity level, peak T-wave heterogeneity level, peak P-wave heterogeneity level, and peak ST-segment heterogeneity level over a period of time to predict risk for cardiac arrhythmias.

6. The method of claim 1, wherein the first receiving step comprises monitoring ECG signals from a patient using a standard 12-lead ECG, wherein each generating step comprises generating a baseline measurement for each lead of the standard 12-lead ECG, and wherein the calculating step produces a residuum signal for each lead of the standard 12-lead ECG.

7. The method of claim 1, wherein the quantifying step quantifies an R-wave heterogeneity by calculating a maximum square root of a second central moment of the residuum signals about the averaged residuum signal occurring within a QRS duration.

8. The method of claim 1, wherein the quantifying step quantifies a T-wave heterogeneity by calculating a maximum square root of a second central moment of the residuum signals about the averaged residuum signal occurring within a JT interval.

9. The method of claim 1, wherein the quantifying step quantifies a P-wave heterogeneity by calculating a maximum square root of a second central moment of the residuum signals about the averaged residuum signal occurring within a PQ interval.

10. The method of claim 1, wherein the quantifying step quantifies an ST-segment heterogeneity by calculating a maximum square root of a second central moment of the residuum signals about the averaged residuum signal occurring within an ST interval.

11. The method of claim 1, wherein the first median beat is computed over a time period between 5 and 10 minutes.

12. The method of claim 1, wherein the second median beat is computed over a time period of about 10 seconds.

13. The method of claim 1, wherein the calculating comprises calculating a difference between each first median beat and the corresponding second median beat.

14. The method of claim 1, wherein the calculating comprises calculating a quotient between each median beat and the corresponding second median beat.

15. The method of claim 1, wherein the first receiving step comprises monitoring ECG signals from a patient using spatially separated leads that comprise at least two pairs of intra-cardiac electrodes.

16. The method of claim 15, wherein the quantifying step quantifies atrial ECG heterogeneity based on a measured atrial depolarization heterogeneity and a measured atrial repolarization heterogeneity, wherein the atrial depolarization heterogeneity and atrial repolarization heterogeneity are measured using the at least two pairs of intra-cardiac electrodes.

17. The method of claim 16, further comprising identifying a peak level of the atrial ECG heterogeneity.

18. The method of claim 17, further comprising determining a trend of the peak atrial ECG heterogeneity over a period of time.

19. The method of claim 17, wherein the step of identifying further comprises using the peak level of the atrial ECG heterogeneity to predict risk for cardiac arrhythmias.

20. An electrocardiogram (ECG) system for quantifying risk of cardiac arrhythmia, comprising:

an input module configured to receive ECG signals from spatially separated leads; and a processor configured to:

generate, for each ECG signal in a first set of ECG signals, a first median beat associated with the morphology of each respective ECG signal of the first set of ECG signals from the spatially separated leads, generate, for each ECG signal in the a second set of ECG signals, a second median beat associated with the morphology of each respective ECG signal of the second set of ECG signals from the spatially separated leads, wherein each second median beat corresponds to a respective one of the first median beats, calculate a residuum signal for each first median beat and the corresponding second median beat, average the residuum signals to produce an averaged residuum signal, and quantify a spatio-temporal heterogeneity of the second set of ECG signals based on the residuum signals and the averaged residuum signal, wherein the spatio-temporal heterogeneity is associated with arrhythmia risk.

21. The system of claim 20, wherein the processor is configured to quantify R-wave heterogeneity, T-wave heterogeneity, P-wave heterogeneity, and ST-segment heterogeneity.

22. The method of claim 20, wherein the processor is configured to quantify at least one selected from the group consisting of R-wave heterogeneity, T-wave heterogeneity, P-wave heterogeneity, and ST-segment heterogeneity.

23. The system of claim 22, wherein the processor is configured to produce a residuum signal for each lead of a standard 12-lead ECG.

24. The system of claim 20, wherein the processor is further configured to quantify an R-wave heterogeneity by calculating a maximum square root of a second central moment of the averaged residuum signal occurring within a QRS duration.

25. The system of claim 20, wherein the processor is further configured to quantify a T-wave heterogeneity by calculating a maximum square root of a second central moment of the averaged residuum signal occurring within a JT interval.

26. The system of claim 20, wherein the processor is further configured to quantify a P-wave heterogeneity by calculating a maximum square root of a second central moment of the averaged residuum signal occurring within a PQ interval.

27. The system of claim 20, wherein the processor is further configured to quantify an ST-segment heterogeneity by calculating a maximum square root of a second central moment of the averaged residuum signal occurring within an ST interval.

28. The system of claim 20, wherein the processor is further configured to determine at least one of peak quantified R-wave heterogeneity, peak T-wave heterogeneity, peak P-wave heterogeneity, and peak ST-segment heterogeneity.

29. The system of claim 28, wherein the processor is further configured to determine a trend of at least one of the peak R-wave heterogeneity, peak T-wave heterogeneity, peak P-wave heterogeneity, and peak ST-segment heterogeneity levels over a period of time.

30. The system of claim 20, wherein the first median beat is computed over a time period between 5 and 10 minutes.

31. The system of claim 20, wherein the second median beat is computed over a time period of about 10 seconds.

32. The system of claim 20, wherein the processor is further configured to calculate a difference between each first median beat and the corresponding second median beat.

33. The system of claim 20, wherein the processor is further configured to calculate a quotient between each first median beat and the corresponding second median beat.

34. The system of claim 20, wherein the spatially separated leads comprise at least two pairs of intra-cardiac electrodes.

35. The system of claim 34, wherein the processor is further configured to quantify an atrial ECG heterogeneity based on a measured atrial depolarization heterogeneity and a measured atrial repolarization heterogeneity, wherein the atrial depolarization heterogeneity and atrial repolarization heterogeneity are measured using the at least two pairs of intra-cardiac electrodes.

36. The system of claim 35, wherein the processor is further configured to determine a peak atrial ECG heterogeneity.

37. The system of claim 36, wherein the processor is further configured to determine a trend of the peak atrial ECG heterogeneity over a period of time.

38. A computer program product stored on a computer readable media, including a set of instructions that, when executed by a computing device, perform a method of quantifying risk of cardiac arrhythmia, comprising:
receiving a first set of electrocardiogram (ECG) signals;
generating, for each ECG signal in the first set of BCG signals, a first median beat associated with the morphology of each respective ECG signal of the first set of ECG signals;
receiving a second set of ECG signals;
generating, for each ECG signal in the second set of ECG signals, a second median beat associated with the morphology of each respective ECG signal of the second set of ECG signals, wherein each second median beat corresponds to a respective one of the first median beats;
calculating a residuum signal for each first median beat and the corresponding second median beat;
averaging the residuum signals to produce an averaged residuum signal; and
quantifying a spatio-temporal heterogeneity of the second set of ECG signals based on the residuum signals and the averaged residuum signal, wherein the spatio-temporal heterogeneity is correlated with arrhythmia risk.

* * * * *

UNITED STATES PATENT AND TRADEMARK OFFICE
CERTIFICATE OF CORRECTION

| | |
|---|---|
| PATENT NO. | : 10,022,060 B2 |
| APPLICATION NO. | : 14/734966 |
| DATED | : July 17, 2018 |
| INVENTOR(S) | : Nearing et al. |

It is certified that error appears in the above-identified patent and that said Letters Patent is hereby corrected as shown below:

In the Claims

In Column 14, Line 57, please replace "a median beat associated with" with --a first median beat associated with--.

In Column 16, Line 2, please replace "between each median beat" with --between each first median beat--.

In Column 18, Line 16, please replace "set of BCG signals," with --set of ECG signals,--.

Signed and Sealed this
Twenty-eighth Day of May, 2019

Andrei Iancu
*Director of the United States Patent and Trademark Office*